United States Patent [19]

Honeyager

[11] Patent Number: 4,924,871
[45] Date of Patent: May 15, 1990

[54] MOTION ARTIFACT DETECTION FOR CONTINUOUS BLOOD PRESSURE MONITOR TRANSDUCER

[75] Inventor: Kevin S. Honeyager, San Antonio, Tex.

[73] Assignee: Colin Electronics Co., Ltd., Japan

[21] Appl. No.: 160,573

[22] Filed: Feb. 26, 1988

[51] Int. Cl.$^5$ .............................. A61B 5/02
[52] U.S. Cl. ..................... 128/672; 128/687
[58] Field of Search ................. 128/670-672, 128/677, 680-690

[56] References Cited

U.S. PATENT DOCUMENTS

| | | | |
|---|---|---|---|
| 3,123,068 | 3/1964 | Bigliano | 128/672 |
| 3,219,035 | 11/1965 | Pressman et al. | 128/672 |
| 3,880,145 | 4/1975 | Blick | 128/672 |
| 4,030,484 | 6/1977 | Kuska et al. | 128/672 |
| 4,185,621 | 1/1980 | Morrow | 128/670 X |
| 4,232,682 | 11/1980 | Veth | 128/671 |
| 4,360,029 | 11/1982 | Ramsey, III | 128/681 |
| 4,423,738 | 1/1984 | Newgard | 128/672 |
| 4,561,447 | 12/1985 | Kawamura et al. | 128/687 |

Primary Examiner—Angela D. Sykes
Attorney, Agent, or Firm—Oliff & Berridge

[57] ABSTRACT

A method for detecting motion artifacts in data obtained from a blood pressure monitoring transducer is provided which prevents erroneous data related to such artifacts from interfering with the accuracy of the blood pressure measurement by way of continuously monitoring the pressure control source which maintains the transducer hold down pressure, and temporarily delaying data acquisition in the event the hold down pressure changes in excess of a predetermined limit.

1 Claim, 3 Drawing Sheets

MOTION ARTIFACT DETECTION FOR CONTINUOUS BLOOD PRESSURE MONITOR TRANSDUCER

FIELD OF THE INVENTION

The present invention relates generally to a method and apparatus for continuous noninvasive measurement of blood pressure. More specifically, the present invention provides a means for detecting motion artifacts and for preventing erroneous data related to said artifacts from interfering with the accuracy of the blood pressure measurement.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in the following U.S. Patents: U.S. Pat. No. 3,123,068 to R. P. Bigliano, U.S. Pat. No. 3,219,035 to G. L. Pressman, P. M. Newgard and John J. Eige, U.S. Pat. No. 3,880,145 to E. F. Blick, U.S. Pat. No. 4,269,193 to Eckerle, and U.S. Pat. No. 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., April 1963, pp. 73-81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. The element that is substantially centered over the artery has a signal output that provides an accurate measure of intraarterial blood pressure. However, for the other transducer elements the signal outputs generally do not provide as accurate a measure of intraarterial blood pressure as the output from the centered element. Generally, the offset upon which systolic and diastolic pressures depend will not be measured accurately using transducer elements that are not centered over the artery.

One of the difficulties encountered in the use of tonometric techniques for monitoring blood pressure is the sensitivity of the pressure sensing elements which makes them extremely susceptible to erroneous detection of motion artifacts as pressure waveforms. Such erroneous detection of motion can cause significant errors in the measured blood pressure. The method of the present invention, described in greater detail below, provides a means for detection of motion artifacts and for preventing pressure waveforms related to motion from erroneously being reported as blood pressure waveforms.

SUMMARY OF THE INVENTION

The present invention relates to a blood pressure monitoring system employing a transducer which comprises an array of individual pressure sensitive elements, each of which elements have at least one dimension smaller than the lumen of the underlying artery in which blood pressure is measured. The elements are of sufficiently small size such that with the array positioned so as to extend across the artery a plurality of elements are located over the artery. For the transducer to properly measure blood pressure it is important that the underlying artery be partially compressed. Specifically, it is important that the artery be flattened by a plane surface so that the stresses developed in the arterial wall perpendicular to the face of the sensor are negligible. This hold down pressure is provided by a pressurizable bellows in the transducer housing which is controlled by an appropriate pressure source to maintain the hold down pressure at the desired level. With the underlying artery properly flattened, the outputs of all of the transducer elements are employed in locating the particular element which is centrally located over the artery. This centered element is then used to measure the blood pressure in the artery.

Movement of the patient's wrist can create a motion artifact which causes the pressure sensing element to provide an erroneous indication of the pressure in the underlying artery. Such movement will also tend to change the pressure in the pressurizable bellows of the transducer. In the method of the present invention, motion is detected by continuously monitoring the pressure control source which maintains the transducer hold down pressure. When motion is detected, data collection from the force sensing element is temporarily delayed to avoid an erroneous indication of blood pressure.

DETAILED DESCRIPTION OF THE PREFERRED EMBODIMENT

Figure 1:
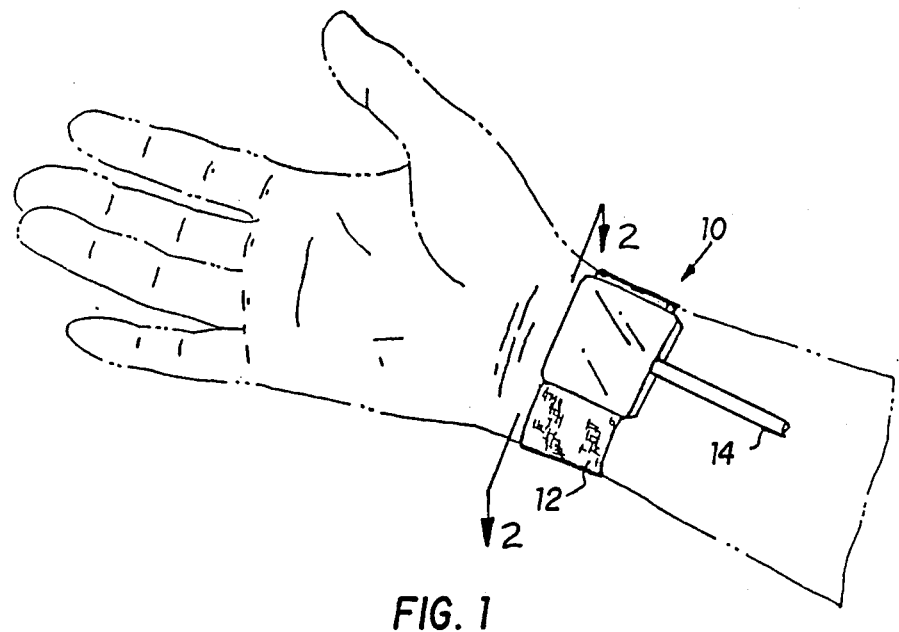
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist at a point overlying the radial artery. The transducer is attached by means of a strap 12 in a manner similar to a conventional wristwatch. A cable assembly 14 connected to the transducer contains electrical cables for carrying electrical signals to and from the transducer. The cable assembly 12 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2:
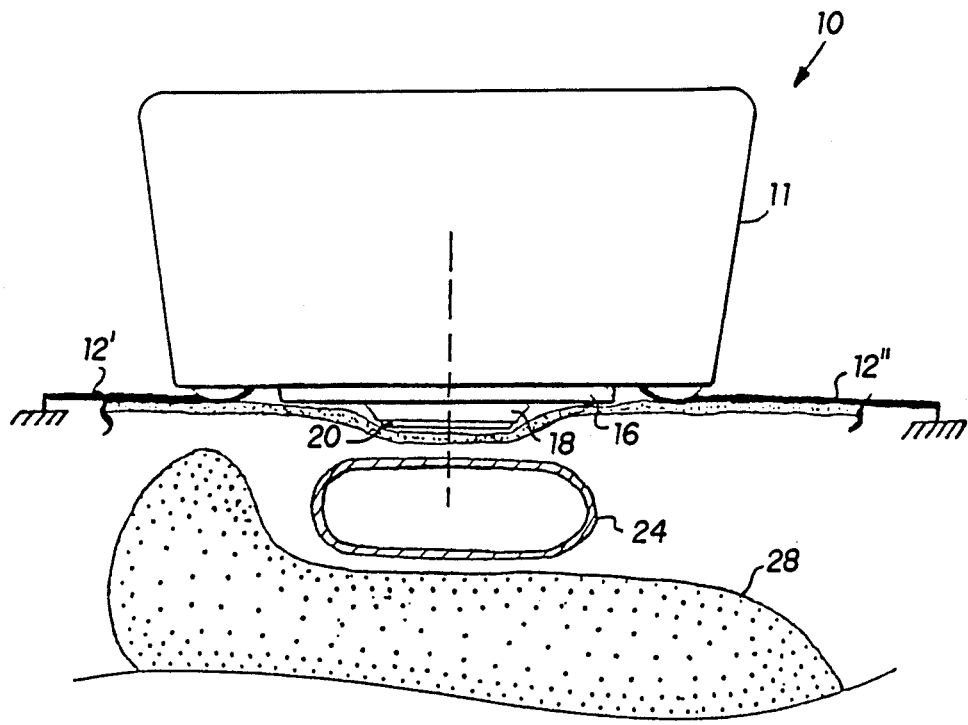
FIG. 2 is a cross sectional side view taken along section lines 2—2 of FIG. 1 illustrating the continuous blood pressure monitor positioned over an artery with the artery being partially flattened in response to pressure applied by a transducer piston assembly.

FIG. 2 is a cross sectional side view, taken along section lines 2—2 of FIG. 1, showing the continuous blood pressure monitor positioned on the patient's wrist at a point overlying the radial artery 24. A transducer piston 16 including a sensor mounting platform 18 is shown protruding from the bottom of the transducer to flatten the artery 24 against the radius bone 28. A sensor 20 is mounted on the lower surface of the sensor mounting platform 18. The sensor 20 comprises a plurality of pressure sensing elements described below. In FIG. 2, the ends 12' and 12" of the strap 12 are shown attached to ground symbols to illustrate that the strap is firmly secured to the patient's wrist. In practice, the strap is secured in generally the same manner as that for a conventional wrist watch.

Figure 3:
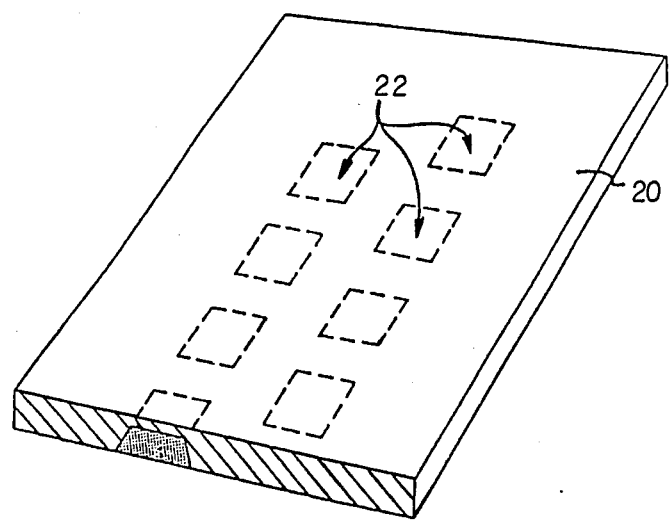
FIG. 3 is a perspective view of an array of pressure sensing elements, etched in a monocrystaline silicon substrate, of the type employed in the pressure transducer of the present invention.

FIG. 3 is a perspective view of the sensor 20 used in the continuous blood pressure monitor of the preferred embodiment. The sensor 20 comprises an array of individual pressure sensing elements 22 which are formed in a thin rectangular monocrystalline silicon substrate using conventional but modern integrated circuit techniques. One method which can be used to form such a silicon chip with regions of predetermined thickness in the chip is described in U.S. Pat. No. 3,888,708 issued to Wise, et al. for "Method for Forming Regions of Predetermined Thickness in Silicon." In the sensor shown in FIG. 3, the individual pressure sensing elements 22 are shown aligned in two rows. This particular arrangement is shown only for purposes of illustration. In practice, various numbers of force sensitive elements can be used, depending on the desired monitoring resolution, and various patterns can be used for arranging the sensing elements within the silicon substrate.

Figure 4:
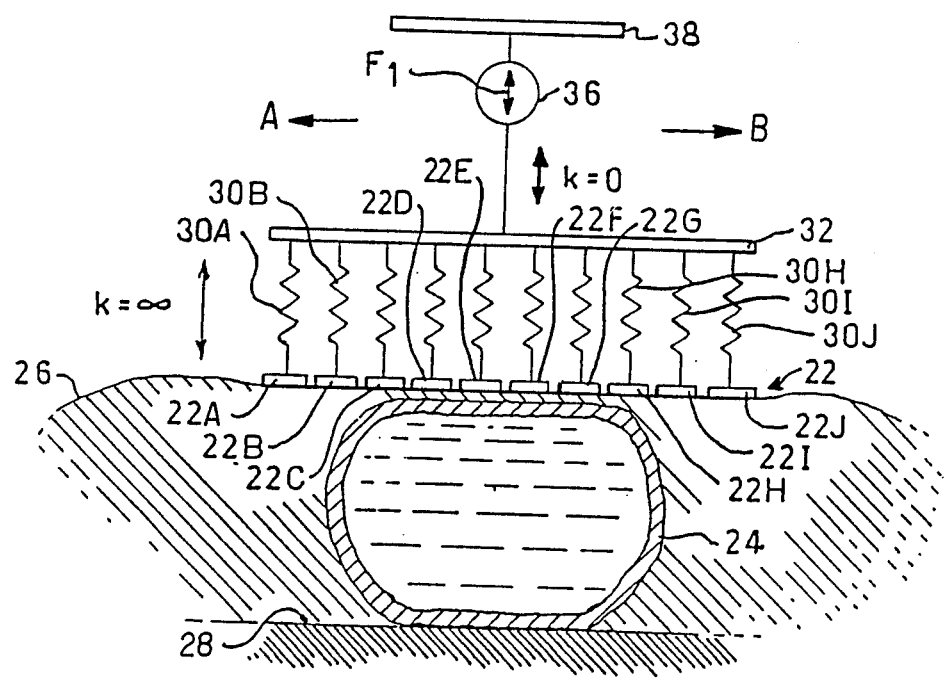
FIG. 4 is a schematic diagram illustrating the force balance between the artery and the multiple transducer elements (arterial riders), with the artery wall properly depressed to give accurate blood pressure readings.

Reference now is made to FIG. 4 wherein a diagrammatic mechanical model is shown which is representative of physical factors to be considered in blood pressure measurements using tonometry techniques. The illustrated model is adapted from that shown in the above-mentioned U.S. Pat. No. 4,269,193, issued to J. S. Eckerle, which by this reference is incorporated for all purposes. An array 22 of individual pressure sensitive elements or transducers 22-A through 22-E, which constitute the arterial riders, is positioned so that one or more of the riders are entirely over an artery 24. The individual riders 22-A through 22-E are small relative to the diameter of the artery 24, thus assuring that a plurality of the riders overlie the artery. The skin surface 26 and artery underlying the transducer must be flattened by application of a hold-down pressure to the transducer. One rider overlying the center of the artery is identified as the "centered" rider, from which rider pressure readings for monitoring blood pressure are obtained. Means for selecting the centered rider are discussed general in the above mentioned U.S. Pat. No. 4,269,193. In addition, an improved means for selecting the best pressure sensing element for measuring blood pressure is disclosed in a patent application entitled "Active Element Selection for Continuous Blood Pressure Monitor Transducer" filed on even date herewith. For present purposes it will be understood that one of the riders, such as rider 22-E, may be selected as the "centered" rider, in which case the remainder of the riders, here riders 22-A through 22-D and 22-F through 22-J, comprise "side plates" which serve to flatten the underlying skin and artery.

Superficial arteries, such as the radial artery, are supported from below by bone which, in FIG. 4, is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. With the illustrated system, the transducer assembly 10 and mounting strap 12, together with air pressure applied to a pressurizable bladder in the transducer assembly, supply the required compression force and hold the riders 22-A through 22-J in such a manner that arterial pressure changes are transferred to the riders which overlie the artery 24. This is illustrated schematically in FIG. 4 by showing the individual riders 22-A through 22-J backed by rider spring members 30-A through 30-J, respectively, a rigid spring backing plate 32, and hold-down force generator 36 between the backing plate 32 and the mounting strap system 38.

If, without force generator 36, the coupling between the mounting strap system 38 and spring backing plate 32 were infinitely stiff to restrain the riders 22-A through 22-J rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-A through 22-J. In the mechanical model the spring constant, k (force per unit of deflection) of the force generator, 36, is nearly zero. Pneumatic loading systems are shown and described in the above-referenced U.S. Pat. Nos. 3,219,035 and 4,269,193, and the Pressman and Newgard IEEE article. In addition, an improved pneumatic loading system is disclosed in a patent application entitled "Pressurization System for Continuous Blood Pressure Monitor Transducer" filed on even date herewith.

In order to insure that the riders 22-A through 22-J flatten the artery and provide a true blood pressure measurement, they must be rigidly mounted to the backing plate 32. Hence, the rider springs 30-A through 30-J of the device ideally are infinitely rigid (spring constant $k = \infty$). It is found that as long as the system operates in such a manner that it can be simulated by rider springs 30-A through 30-J having a spring constant on the order of about ten times the corresponding constant for the artery-skin system, so that the deflection of riders 22-A through 22-J is small, a true blood pressure measurement may be obtained when the correct hold-down pressure is employed.

Figure 5:
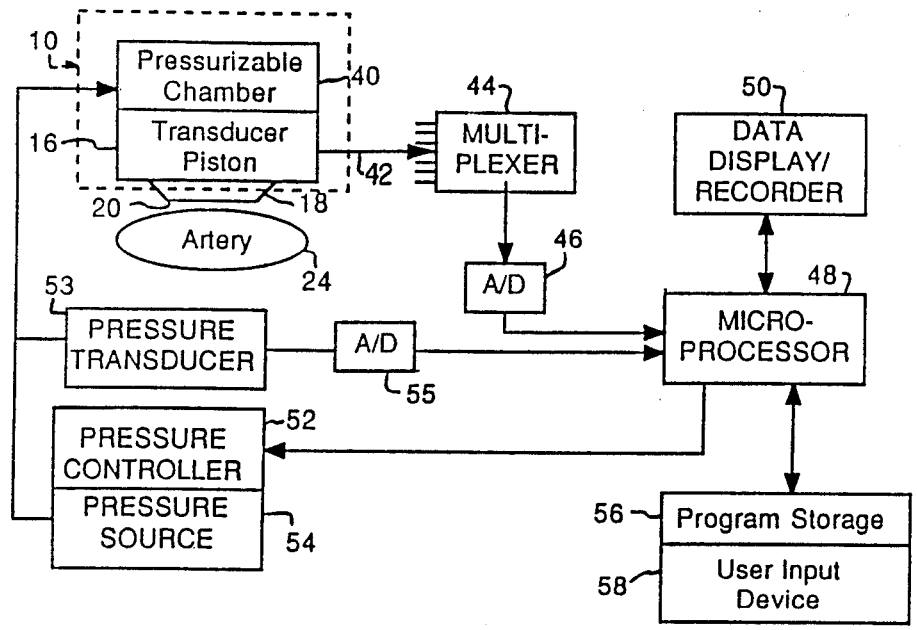
FIG. 5 is a simplified block diagram of the system components for monitoring a plurality of force sensing elements to for measuring blood pressure in an underlying artery.

Referring to FIG. 5, a simplified illustration of the transducer assembly 10 is shown to include a transducer piston 16, a pressurizable chamber 40 and a sensor 20. The output of the individual pressure sensors (not shown) on the sensor 20 are connected by appropriate electrical wiring 42 to the input of a multiplexer 44. From the multiplexer, the signals are digitized by an analog-to-digital (A-D) converter 46, and the digitized signals are supplied to a microprocessor 48. Output from the microprocessor 48 is supplied to data display and recorder means 50 which may include a recorder, cathode ray tube monitor, a solid state display, or any other suitable display device. Also, the output from the microprocessor is provided to the pressure controller 52 which controls a pressure source 54 to maintain the appropriate hold down pressure for the transducer piston 16. Operation of the microprocessor can be controlled by a program contained in program storage 56 or by user input from the user input device, which can be in the form of a keyboard or other interface device. The appropriate hold down pressure in the pressurizable chamber 40 of the transducer assembly is maintained by a pressure feedback signal which is provided by a pressure transducer 53 which is connected to the output of the pressure source 54. The pressure transducer 53 provides an electrical output signal which is proportional to the pressure in the pressurizable chamber 40. The electrical output signal of the pressure transducer 53 is digitized by an A-D converter 55 and is supplied to the microprocessor 48.

Figure 6:
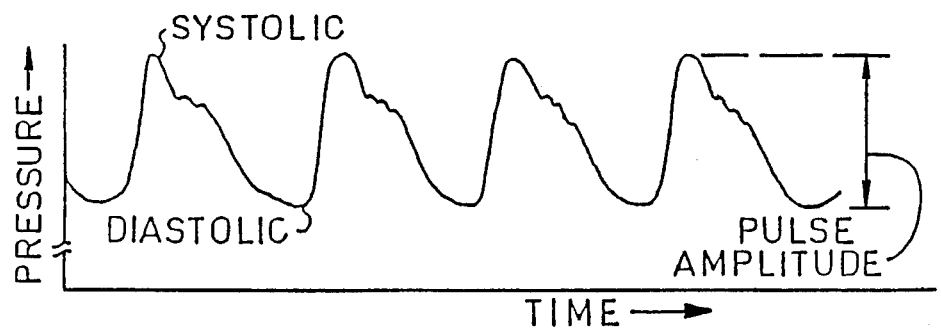
FIG. 6 is an illustration of a signal waveform obtained from one of the pressure sensitive elements on the sensor employed in the present invention.

Reference is now made to FIG. 6 which illustrates the signal waveform of the output from one of the pressure sensitive elements 22-A through 22-J which overlies artery 24. Other elements of the transducer array which overlie the artery will have waveforms of similar shape. With a correct hold-down pressure and correct selection of the "centered" arterial rider (i.e., the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat. A method for using the waveform produced by the centered element for measuring blood pressure in the underlying artery is diclosed in the above-incorporated U.S. Pat. No. 4,269,193, and are not repeated herein.

The pressure inside the pressurizable chamber 40 shown in FIG. 5 varies over a range from approximately 0 mm Hg to approximately 300 mm Hg in response to pressurized gas provided by the pressure source 54. However, once the optimum hold down pressure in the pressurizable chamber has been achieved, e.g., 70 mm Hg, the pressure therein will normally remain relatively constant. Typically the pressure will vary less than 10 mm Hg after the hold down pressure has been stabilized. Physical disturbances, such as the movement of the patient's arm can lead to erroneous pressure signals being detected by the pressure sensing elements. Such movements also tend to move the transducer from optimum contact pressure with the patient's arm, and, therefore, such motion can be detected as a change in the pressure in the pressurizable chamber 40 of the transducer assembly. Such a pressure change will be detected by the pressure transducer 53 and provided to the microprocessor via the A-D converter 55. The output of the pressure transducer can, therefore, be used as an indirect indication of motion.

During the time that motion is detected, it is important to interrupt the collection of data from the pressure sensing element to maintain maximum accuracy in the blood pressure measurement. In the method of the present invention, data collection is interrupted temporarily during the time that the output signal of the pressure transducer 53 indicates a pressurization change of more than a predetermined limit, e.g., 10 mm of Hg, in the pressurizable bellows of the transducer assembly 10. In the preferred embodiment of the present method, data collection is interrupted for a time period of three seconds upon detection of a pressurization change related to motion. Obviously, this pressure limit and the specific time that data collection is interrupted can be varied to make the monitoring system more or less sensitive to the effects of motion artifacts on the measurement of blood pressure.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by the appended claims.

I claim:

1. A method for rejecting motion artifacts in data obtained from a blood pressure monitor transducer, comprising the steps of:

attaching a transducer to a person's wrist, said transducer comprising a pressurizable bellows and a sensor having a plurality of pressure sensing elements thereon, said sensor being positioned over an artery in said wrist to allow at least one of said pressure sensing elements to produce a pulse amplitude output signal indicative of the pulse waveform in said artery;

pressurizing said pressurizable bellows to a predetermined hold down pressure;

monitoring the pressure in said pressurizable bellows to detect a change therein above a predetermined limit, said predetermined limit being indicative of motion of said patient; and interrupting the collection of data from said pressure sensing elements for a predetermined time upon detection of a change in pressure above said predetermined limit.

* * * * *